United States Patent [19]
Aranyi et al.

[11] Patent Number: 5,928,251
[45] Date of Patent: Jul. 27, 1999

[54] OCCLUSION CLAMP AND OCCLUSION CLAMP APPLICATOR

[75] Inventors: Cathy Aranyi, Easton; Robert J. DeSantis, West Redding; Richard Yagami, Bridgewater, all of Conn.

[73] Assignee: United States Surgical Corporation, Norwalk, Conn.

[21] Appl. No.: 08/932,685

[22] Filed: Sep. 18, 1997

[51] Int. Cl.⁶ ..................................................... A61B 17/00
[52] U.S. Cl. ............................................................ 606/142
[58] Field of Search ..................................... 606/142, 148, 606/151, 157, 158, 205–208; 227/901, 902

[56] References Cited

U.S. PATENT DOCUMENTS

| | | |
|---|---|---|
| 3,506,012 | 4/1970 | Brown . |
| 3,518,993 | 7/1970 | Blake . |
| 3,827,277 | 8/1974 | Weston . |
| 3,958,576 | 5/1976 | Komiya . |
| 4,038,987 | 8/1977 | Komiya . |
| 4,174,715 | 11/1979 | Hasson . |
| 4,192,315 | 3/1980 | Hilzinger et al. . |
| 4,241,734 | 12/1980 | Kandel et al. . |
| 4,269,190 | 5/1981 | Behney . |
| 4,367,746 | 1/1983 | Derechinsky . |
| 4,374,523 | 2/1983 | Yoon . |
| 4,660,558 | 4/1987 | Kees, Jr. . |
| 4,681,107 | 7/1987 | Kees, Jr. . |
| 4,706,668 | 11/1987 | Backer . |
| 4,777,949 | 10/1988 | Perlin . |
| 4,932,955 | 6/1990 | Merz et al. . |
| 4,943,298 | 7/1990 | Fujita et al. . |
| 4,961,743 | 10/1990 | Kees, Jr. et al. . |
| 5,053,045 | 10/1991 | Schmidt et al. . |
| 5,074,870 | 12/1991 | von Zeppelin . |
| 5,242,456 | 9/1993 | Nash et al. . |
| 5,304,183 | 4/1994 | Gourlay et al. . |
| 5,312,426 | 5/1994 | Segawa et al. . |
| 5,342,373 | 8/1994 | Stefanchik et al. . |
| 5,368,600 | 11/1994 | Failla et al. . |
| 5,520,701 | 5/1996 | Lerch . |
| 5,522,823 | 6/1996 | Kuntz et al. . |
| 5,569,274 | 10/1996 | Rapacki et al. . |
| 5,618,307 | 4/1997 | Donlon et al. . |

FOREIGN PATENT DOCUMENTS

| | | |
|---|---|---|
| WO 93/0972 | 5/1993 | WIPO . |
| WO 93/18712 | 9/1993 | WIPO . |

*Primary Examiner*—Gary Jackson
*Assistant Examiner*—Vikki Trinh

[57] ABSTRACT

An occlusion clamp and an applicator for applying the occlusion clamp to body tissue is provided. The occlusion clamp applicator includes a housing having a proximal end having a first opening, a distal end having a second opening, and a pair of finger gripping members. The housing defines a channel which extends between the first and second openings. A plunger is partially positioned within the channel and extends through the first opening. The distal end of the plunger is operably connected to a jaw mechanism which is also slidably positioned within the channel. The jaw mechanism includes a pair of resilient shank portions, each having a distally located jaw member which extends through the second housing opening. Each shank portion also includes a cam surface which engages the distal end of the channel when the plunger is retracted to move the jaw members from a position in spaced relation with each other to a position relatively close in relation with each other. Each jaw member includes a slot having converging sidewalls which intersect at an apex. An occlusion clamp is supported between the jaw members and includes a base portion and a pair of legs extending therefrom. Each leg includes a pair of parallel proximal portions, a pair of cross-over portions, and a pair of clamping portions. Each proximal portion includes a dimpled section configured to receive the sidewalls of the slot in the jaw members. When the jaw members are in the position in spaced relation with each other, the apex protrudes slightly into the dimpled section of the clamp to prevent inadvertent separation of the clamp and the applicator.

25 Claims, 5 Drawing Sheets

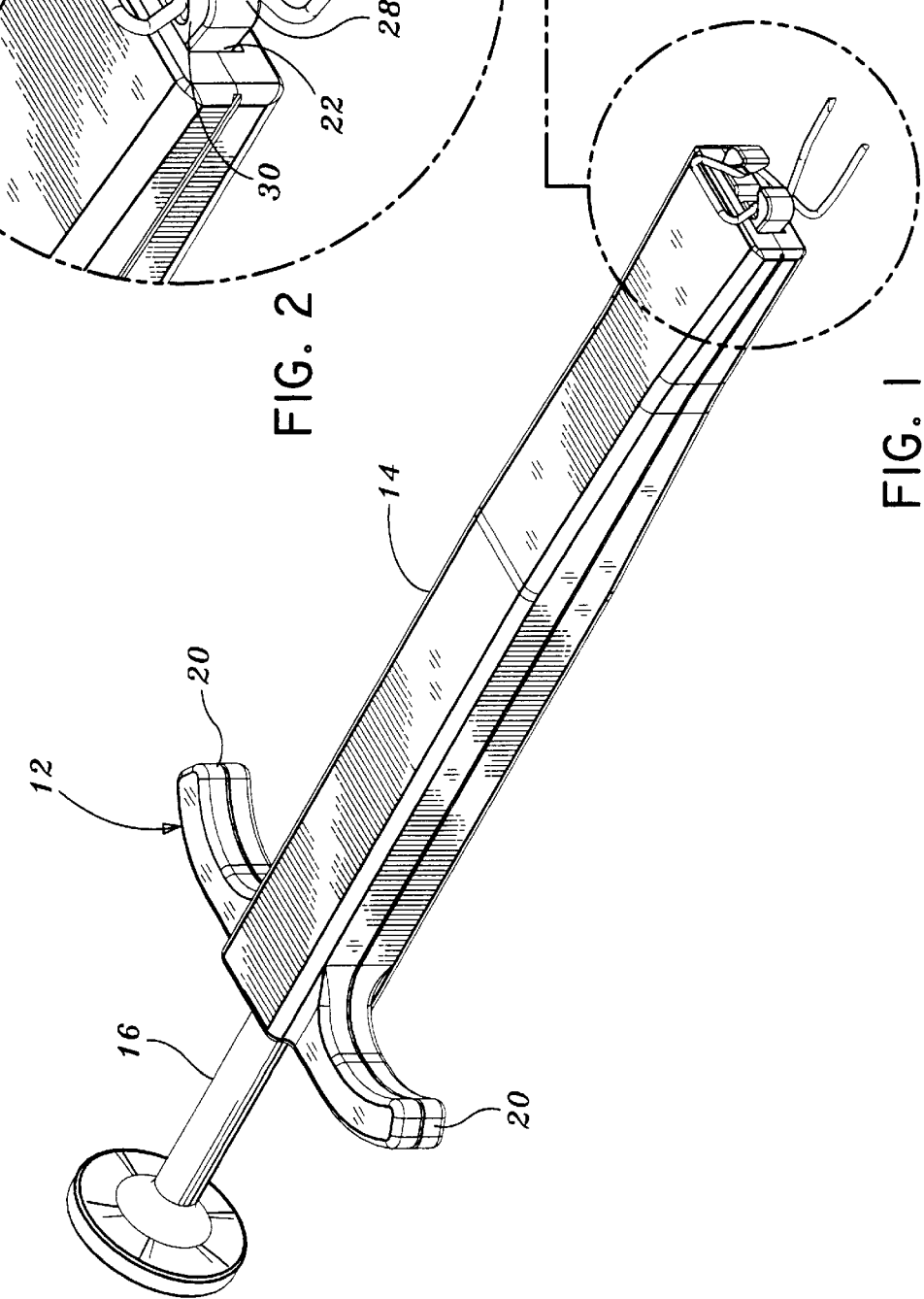

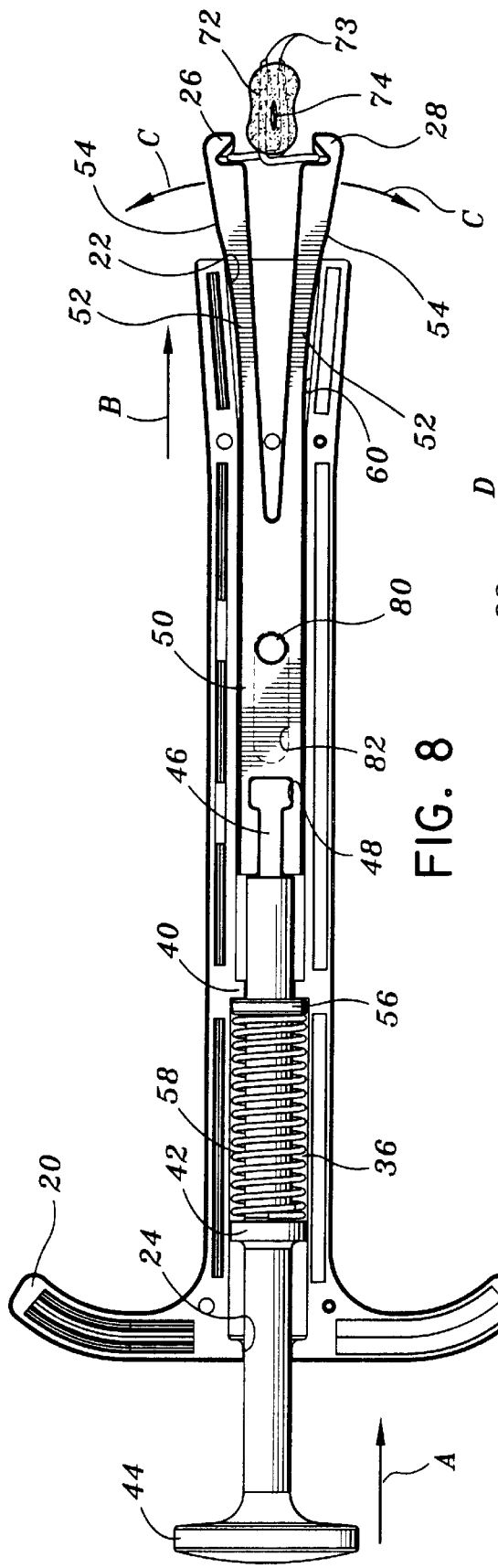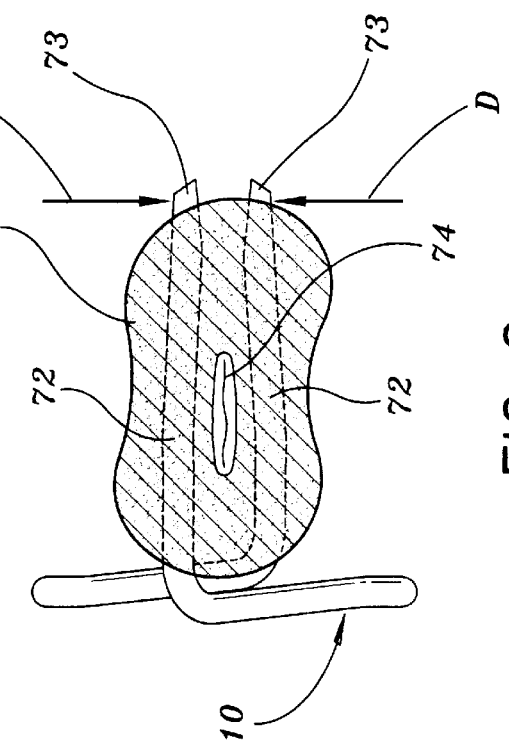
FIG. 8
FIG. 9

OCCLUSION CLAMP AND OCCLUSION CLAMP APPLICATOR

BACKGROUND

1. Technical Field

The present disclosure relates to an occlusion clamp and applicator for applying the occlusion clamp to body tissue. More specifically, the present disclosure relates to an occlusion clamp and applicator having few moving parts particularly suited for coronary bypass procedures.

2. Background of Related Art

Occlusion clamps and applicators for applying occlusion clamps to tissue are known in the art. Typically, occlusion clamps are used during a variety of surgical procedures to isolate an area which requires surgical repair. For example, during coronary artery bypass grafting occlusion clamps are used to isolate the heart and the coronary blood vessels by placing an occlusion clamp on the ascending aorta. Occlusion clamps are also used extensively during neurosurgical procedures to isolate a cerebral aneurysm from the cerebral artery. Such known occlusion clamps and applicators for applying occlusion clamps to tissue are complex and are susceptible to inadvertent separation of the occlusion clamp from the occlusion clamp applicator.

U.S. Pat. No. 4,367,746 to Derechinsky discloses an applicator for applying clips to blood vessels. The applicator includes a rectilinear tube having a coaxial rod extending therethrough. The distal end of the rod includes a hook adapted to support a clip. A handle and operating mechanism are connected to a proximal end of the tube and rod and are operable to reciprocate the tube relative to the rod. The tube and rod are biased relative to each other such that a clip supported on the hook is partially retained within the tube in a compressed and open position. Upon actuation of the applicator, the tube is retracted from about the clip to allow the clip to return to a normally closed position. If the clip is not adequately clamped about tissue when the actuator is released, it is likely that the clip will become disengaged from the hook and fall into the body adjacent the surgical site.

This is especially true during procedures which require the instrument to be partially rotated about its longitudinal axis during application of the clamp.

Accordingly, a need exists for an occlusion clamp and clamp applicator which reduces the likelihood of inadvertent separation of the occlusion clamp and clamp applicator and is easy to use and to manufacture.

SUMMARY

In accordance with the present disclosure, an occlusion clamp and an applicator for applying the occlusion clamp to body tissue is provided. The occlusion clamp applicator includes a housing having a proximal end having a first opening, a distal end having a second opening, and a pair of finger gripping members extending radially outwardly from the exterior of the housing. The housing defines a channel which extends between the first and second openings. A plunger is partially positioned within the channel and extends through the first opening. The distal end of the plunger is operably connected to a jaw mechanism which is also slidably positioned within the channel. The jaw mechanism includes a pair of resilient shank portions, each having a distally located jaw member which extends through the second housing opening. Each shank portion also includes a cam surface which engages the distal end of the channel when the plunger is retracted to move the jaw members from a position in spaced relation with each other to a position relatively close in relation with each other. Each jaw member includes a slot having converging sidewalls which intersect at an apex. The slots are configured to support an occlusion clamp.

An occlusion clamp usable with the presently disclosed clamp applicator includes a base portion and a pair of legs extending therefrom. Each leg includes a pair of parallel proximal portions, a pair of cross-over portions, and a pair of clamping portions. Each proximal portion includes a dimpled section configured to receive the converging sidewalls of the slot in the jaw members of the presently disclosed clamp applicator. When the jaw members are in the position in spaced relation with each other, the apex protrudes slightly into the dimpled section of the clamp to prevent inadvertent separation of the clamp and the applicator.

DESCRIPTION OF THE DRAWINGS

Various preferred embodiments are described herein with reference to the drawings, wherein:

FIG. 1 is a perspective view of one embodiment of the presently disclosed occlusion clamp and clamp applicator;

FIG. 2 is an enlarged view of the distal end of the occlusion clamp and clamp applicator shown in the indicated area of detail of FIG. 1;

FIG. 8 is a top view of the occlusion clamp and clamp applicator shown in FIG. 1 with the top housing half-section removed, the jaws in an advanced position, and the occlusion clamp in the closed (clamped) position about a vessel; and FIG. 9 is a top view of the occlusion clamp shown in FIG. 7 disengaged from the clamp applicator and positioned about a vessel.

DETAILED DESCRIPTION OF PREFERRED EMBODIMENTS

Figure 3:
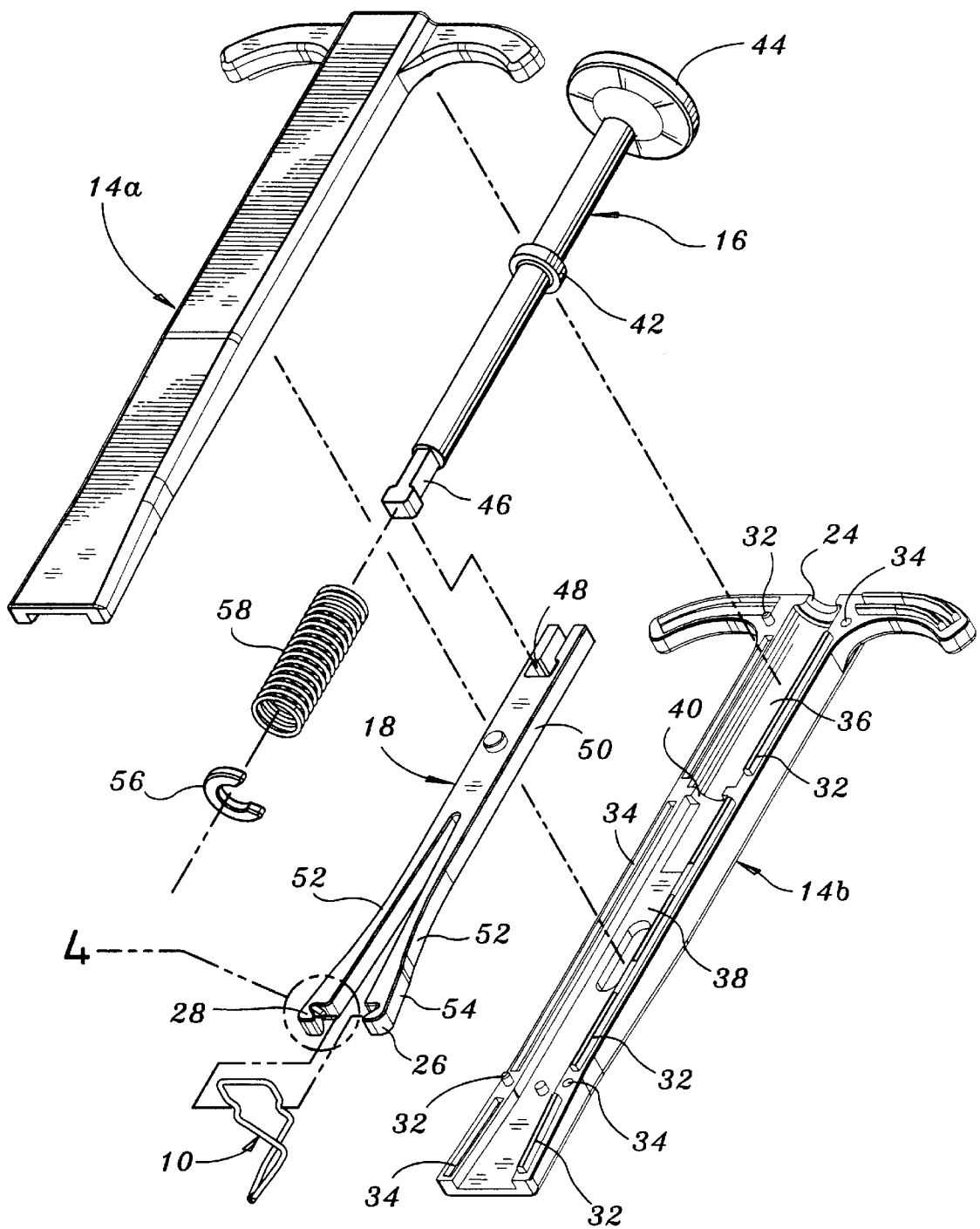
FIG. 3 is a perspective view with parts separated of the occlusion clamp and clamp applicator shown in FIG. 1.

Preferred embodiments of the presently disclosed occlusion clamp and clamp applicator will now be described in detail with reference to the drawings, in which like reference numerals designate identical or corresponding elements in each of the several views.

FIGS. 1 and 2 illustrate the presently disclosed occlusion clamp and clamp applicator shown generally as 10 and 12, respectively. Briefly, clamp applicator 12 includes housing 14, plunger 16 and jaw mechanism 18. Housing 14 is formed having a pair of rearwardly located finger gripping members 20 and a forwardly and a rearwardly located opening 22 and 24 (FIG. 3), respectively. Plunger 16 extends through rearward opening 24. Jaw mechanism 18 is positioned within housing 14 and has a distal end which extends through forward opening 22 and outside housing 14. The distal end of jaw mechanism 18 includes a pair of resilient jaw members 26 and 28. Each jaw member 26 and 28 includes a slot 30 configured and dimensioned to engage the body of a clamp 10. Slots 30 have a pair of converging sidewalls 27 that intersect at an apex 29. See FIG. 4.

Figure 4:
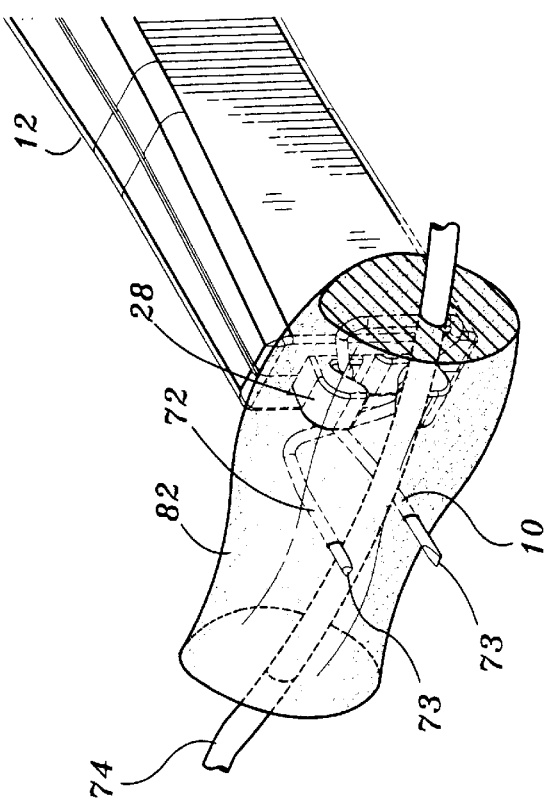
FIG. 4 is an enlarged view of the distal end of the jaw mechanism of the occlusion clamp applicator shown in the indicated area of detail of FIG. 3.

Referring to FIG. 3, housing 14 is preferably constructed from molded half-sections 14a and 14b which are fastened together using pins and/or tabs 32 on one of the housing half-sections and identically configured openings 34 formed in the other of the housing half-sections. Tabs and/or pins 32 are snap-fit into openings 34 to secure the housing half-sections together. Preferably, each housing half-section includes both pins 32 and openings 34 spaced along its periphery. Alternately, other fastening methods may be used to attach the housing half-sections together, e.g., adhesives, screws, sonic welding, etc. Housing half-sections 14a and 14b define a channel within housing 14 which includes rearward channel portion 36 and forward channel portion 38. Forward channel portion 38 includes a proximal rectilinear section and a distal section that gradually increases in width toward its forward end, i.e., each sidewall defining channel portion 38 tapers outwardly towards the forward end of housing half-sections 14a and 14b. Annular shoulder 40 separates forward and rearward channel portions 36 and 38.

Plunger 16 includes a cylindrical body portion having an annular flange 42 formed along a midsection thereof. An actuator member 44, preferably configured for engagement with a user's thumb, is formed on a rearward end of plunger 16 and an attachment member 46 is formed on the forward end of plunger 16. Attachment member 46 and/or actuator member 44 may be monolithically formed with plunger 16 or formed separately and attached thereto. Attachment member 46 is configured to be fixedly received within a correspondingly shaped interlocking slot 48 formed in the rearward end of jaw mechanism 18. Although illustrated as being T-shaped, other interlocking configurations are contemplated, e.g., bulbous tip.

Figure 5:
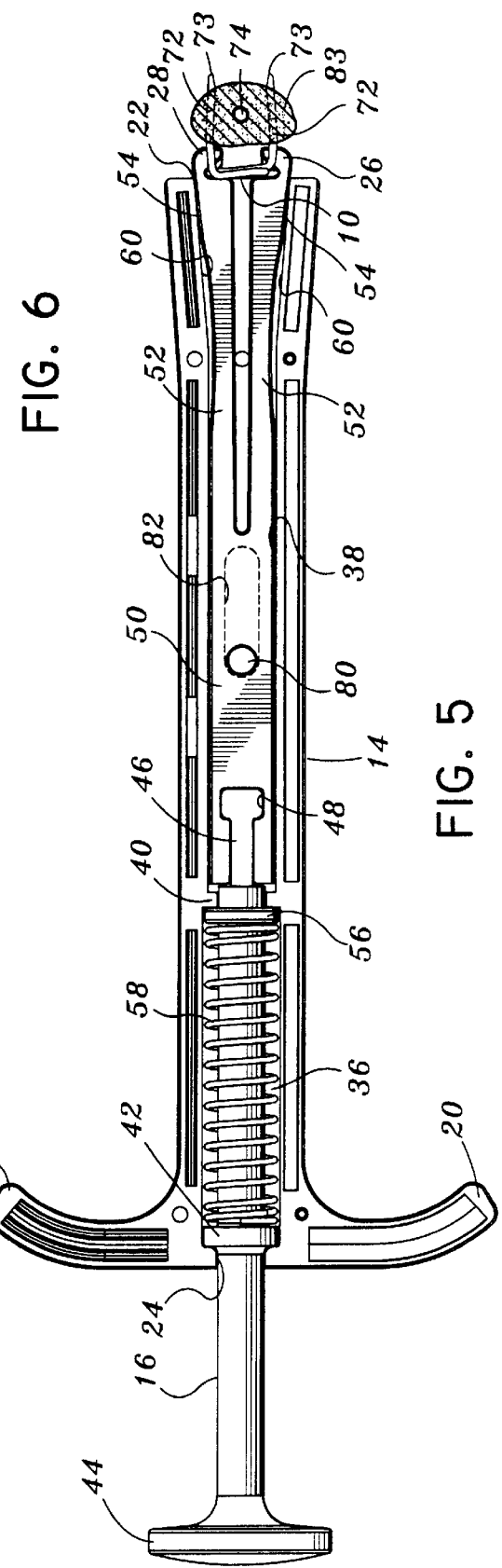
FIG. 5 is a top view of the occlusion clamp and clamp applicator shown in FIG. 1 with the top housing half-section removed, the jaws in a retracted position, and the occlusion clamp in the open position located about a vessel.

Jaw mechanism 18 includes body portion 50 and a pair of forwardly extending resilient shank portions 52. Interlocking slot 48 is formed in the rearward end of body portion 50 and is configured to fixedly receive attachment member 46 of plunger 16, as discussed above. Resilient shank portions 52 of jaw mechanism 18 extend forwardly from body portion 50 and are angled outwardly in an unbiased state. Jaw members 26 and 28 are formed on the distal end of shank portions 52. Each shank portion 52 also includes a cam surface 54 positioned to engage the forward end of forward channel portion 38. The distance between cam surfaces 54 in the unbiased state is greater than the width of the distal end of channel portion 38, such that when jaw mechanism 18 is retracted into channel portion 38, shank portions 52 are biased inwardly to move jaw members 26 and 28 from a spaced configuration to a configuration in which jaw members 26 and 28 are in a relatively closer relation. Referring also to FIG. 5, plunger 16 and jaw mechanism 18 are positioned within housing 14 such that annular flange 42 is slidably positioned within rearward channel portion 36 and jaw mechanism 18 is slidably positioned within forward channel 38. Annular flange 42 has a larger outside diameter than the inside diameter of housing opening 24 such that engagement between annular flange 42 and the rearward end of channel portion 36 defines the fully retracted position of plunger 16. Optionally, a C-clip 56 is positioned about plunger 16 located, within channel portion 36 to abut annular shoulder 40. Biasing member 58, which is preferably a coil spring, is positioned about plunger 16 in channel portion 36 between annular flange 42 and C-clip 56 to urge plunger 16 to the fully retracted position.

Figure 6:
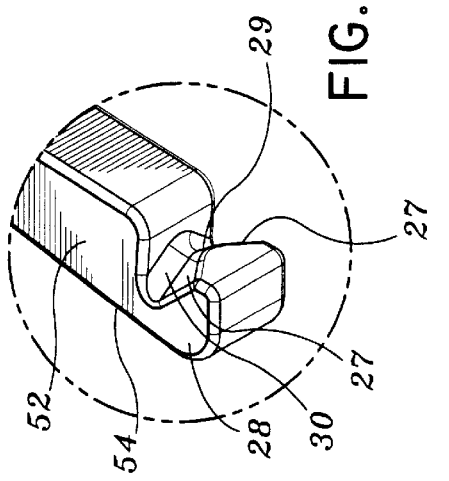
FIG. 6 is an enlarged perspective view of the distal end of the occlusion clamp and clamp actuator shown in FIG. 5.
Figure 7:
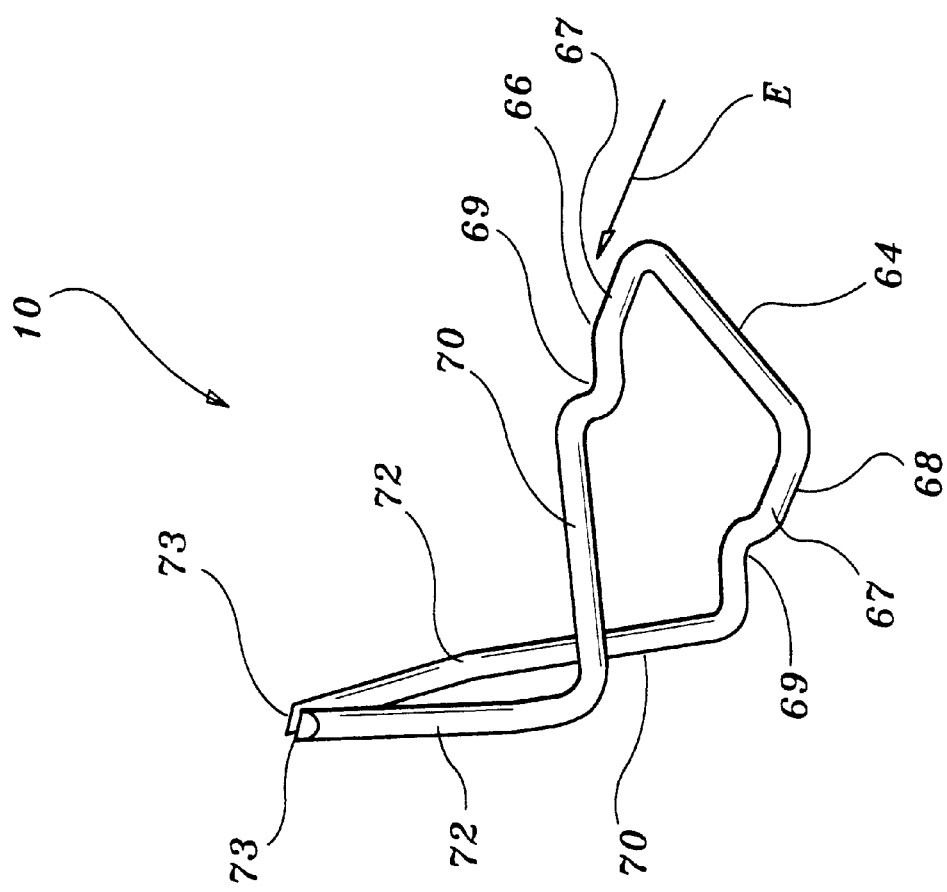
FIG. 7 is an enlarged perspective view of the occlusion clamp shown in FIG. 1.

Referring to FIG. 7, occlusion clamp 10 is preferably constructed from a single length of spring wire deformed to a shape having a base portion 64, a first leg 66 extending from one end of base portion 64, and second leg 68 extending from the other end of base portion 64. Each leg 64 and 66 includes a proximal portion 67 having a dimpled section 69, a central cross-over portion 70, and a distal clamping portion 72. Proximal portions 67 are parallel to each other and perpendicular to base portion 64. Dimpled sections 69 are dimensioned to receive converging sidewalls 27 and 29 of slot 30 (FIG. 4) of jaw members 26 and 28 to facilitate proper positioning of clamp 10 between jaw 26 and 28. The distal end 73 of each clamping portion 72 is sharpened to permit penetration of clamping portions 72 through body tissue about a vessel 74 (See FIGS. 5 and 6). The tips can also be semi-sharp, shaped as a chisel.

Referring again to FIGS. 5 and 6, biasing member 58 urges plunger 16 to the retracted position to retract jaw mechanism 18 into channel 38. In the retracted position, shank portions 52 of jaw mechanism 18 are located substantially within channel portion 38 with cam surfaces 54 of shank portions 52 in engagement with outwardly tapered walls 60 of channel portion 38. In the retracted position, jaw members 26 and 28 extend through opening 22 in housing 14. Because the distance between the cam surfaces 54 of shank portions 52 in the unbiased condition is greater than the width of the forward end of channel 38, shank portions 52 are urged inwardly to move jaw members 26 and 28 inwardly toward each other. With a clamp 10 supported between jaw members 26 and 28, inward movement of jaw members 26 and 28 causes corresponding inward movement of proximal portions 67 (FIG. 7) of clamp 10 to move distal clamping portions 72 of occlusion clamp 10 away from each other to the spaced configuration.

Referring to FIGS. 8 and 9, when plunger 16 is moved longitudinally in the direction indicated by arrow "A", biasing member 58 is compressed within channel 36 between annular shoulder 42 and C-clip 56 and jaw mechanism 18 is advanced longitudinally in the direction indicated by arrow "B" to advance cam surfaces 54 from forward channel portion 38 through opening 22. Guide pins 80 (only one is illustrated) formed on opposite sides of body portion 50 of jaw mechanism 18 are dimensioned to be received in guide slots 82 formed in housing half-sections 14a and 14b and restrict jaw mechanism 18 to linear movement within channel portion 38. Guide slots 82 may extend through housing half-sections 14a and 14b, or may be formed only as grooves in housing half-sections 14a and 14b. As jaw mechanism 18 is advanced longitudinally, resilient shank portions 52 are advanced along channel portion 38 through opening 22 disengaging cam surfaces 54 from tapered walls 60 and allowing resilient shank portions 52 to move to their unbiased state and jaw members 26 and 28 to move apart to the spaced configuration as indicated by arrow "C" in FIG. 8. In the spaced configuration of jaw members 26 and 28, apexes 29 in slot 30 extend slightly into dimple sections 69 to assist in retaining clamp 10 between jaws 26 and 28. In the spaced configuration, proximal portions 72 of occlusion clamp 10 move apart to allow clamping portions 72 of occlusion clamp 10 to move together to a clamped position as indicated by arrow "D" in FIG. 9. After clamp 10 is properly clamped about a vessel 74, applicator 12 can be slid over clamp 10. The force of clamp 10 about vessel 74 is sufficient to overcome the small frictional force required to disengage apexes 29 from dimpled sections 68.

To apply another clamp 10 about a vessel, plunger 16 is advanced to move the jaw members 26, 28 further distally of housing 44 to allow the jaw members to flex outwardly to a position spread further apart. In this position, slots 30 of jaw members 26 and 28 can be slid downwardly over base portion 64 of clamp 10 in a direction parallel to proximal leg portions 67, as indicated by arrow "E" in FIG. 7, to position slots 30 of jaw members 26 and 28 in alignment with dimpled sections 69 of clamp 10. It is noted that the distance between apexes 29 of slots 30 in the outwardly flexed position is equal to or slightly smaller than the distance between the outer surfaces of proximal leg portions 67, such that even when the jaw members 26 and 28 are in the advanced spread apart position, as illustrated in FIGS. 8 and 9, clamp 10 is prevented from falling from between the jaw members. Plunger 16 is then released, thereby retracting jaw members 26 and 28 to the position illustrated in FIG. 5 to spread apart clamp portions 72. Clamp 10 can then be applied to tissue as described above.

Occlusion clamp 10 and clamp applicator 12 may be used to perform a variety of surgical procedures. For example, the occlusion clamp 10 and clamp applicator 12 may be used to clamp the coronary artery during bypass surgical procedures. As illustrated in FIGS. 5, 6, 8 and 9, the sharpened end of each clamping portion 72 is positioned to penetrate tissue 83 located about vessel 74 to be clamped, e.g., coronary artery. By positioning clamp portions 72 in tissue 83 located about the coronary artery 74, tissue 83 acts as a cushion between clamping portions 72 and coronary artery 74 to prevent inadvertent vessel damage.

It will be understood that various modifications may be made to the embodiments disclosed herein. For example, the plunger and the jaw mechanism can be monolithically formed. Further, the shape of the cam surfaces on the shank portions of the jaw mechanism and the shape of the forward channel portion in the housing may include any configuration which produces the desired result of moving the jaw members from position in spaced relation to positions in relatively close relation. Therefore, the above description should not be construed as limiting, but merely as exemplifications of preferred embodiments. Those skilled in the art will envision other modifications within the scope and spirit of the claims appended thereto.

What is claimed is:

1. An occlusion clamp applicator comprising:
    a housing having a proximal end and a distal end, the housing defining a channel therein;
    a plunger positioned within the channel and extending from the proximal end of the housing, the plunger being longitudinally movable between retracted and advanced positions;
    a plunger positioned within the channel and extending from the proximal end of the housing, the plunger being longitudinally movable between retracted and advanced positions;
    a jaw mechanism having first and second resilient shank portions and including first and second jaw members, one of the jaw members being supported at a distal end of each of the resilient shank portions, the jaw mechanism being positioned at least partially within the channel and being operably connected and longitudinally movable with the plunger; and
    an engaging surface operably associated with the jaw mechanism and positioned to move the jaw members between a position in spaced relation with each other and a position in relative close relation with each other in response to movement of the plunger between the retracted and advanced positions.

2. An occlusion clamp applicator according to claim 1, wherein at least one sidewall of the channel defines the engaging surface.

3. An occlusion clamp applicator according to claim 2, wherein the at least one sidewall of the channel defining the engaging surface tapers outwardly towards the distal end of the channel.

4. An occlusion clamp applicator according to claim 3, wherein the at least one sidewall includes a pair of sidewalls, each of the sidewalls tapering outwardly towards the distal end of the channel.

5. An occlusion clamp applicator according to claim 1, further including a biasing member operably engaging the plunger, the biasing member urging the plunger toward the retracted position.

6. An occlusion applicator according to claim 5, wherein the biasing member includes a coil spring.

7. An occlusion clamp applicator according to claim 1, wherein the housing includes a pair of finger gripping members positioned at a proximal end thereof.

8. An occlusion clamp applicator according to claim 7, wherein the plunger includes an actuator member supported at a proximal end thereof.

9. An occlusion clamp applicator according to claim 1, wherein the jaw members each include a slot configured to support a clamp therebetween.

10. An occlusion clamp applicator according to claim 9, wherein each slot includes angled sidewalls which intersect at an apex.

11. An occlusion clamp applicator comprising:
    a) a base portion having a longitudinal axis and first and second ends;
    b) a proximal portion extending from each end of the base portion at an angle substantially perpendicular to the longitudinal axis of the base portion, each proximal portion extending parallel to the other proximal portion;
    c) a cross-over portion extending from the distal end of each of the proximal portions; and
    d) a clamping portion extending from the distal end of each cross-over portion.

12. A resilient occlusion clamp according to claim 11, wherein the distal end of each clamping portion includes a tissue penetrating tip.

13. A resilient occlusion clamp according to claim 11, wherein each proximal portion includes a dimpled section configured to receive a portion of a jaw member of an occlusion clamp applicator.

14. A surgical instrument comprising:
    a) an occlusion clamp applicator including:
        i) a housing having a proximal end and a distal end, the housing defining a channel therein;
        ii) a plunger positioned within the channel and extending from the proximal end of the housing, the plunger being longitudinally movable between retracted and advanced positions;
        iii) a jaw mechanism having first and second resilient shank portions and including first and second jaw members, one of the jaw members being supported at a distal end of each of the resilient shank portions, the jaw mechanism being positioned at least partially within the channel and being operably connected and longitudinally movable with the plunger; and
        iv) an engaging surface operably associated with the jaw mechanism and positioned to move the jaw members between a position in spaced relation with each other and a position in relative close relation with each other in response to movement of the plunger between the retracted and advanced positions;

b) a resilient occlusion clamp supported by the jaw members, the occlusion clamp including:
   i) a base portion having first and second ends;
   ii) a proximal portion extending from each end of the base portion, each proximal portion being substantially perpendicular to the base portion and extending parallel to the other proximal portion;
   iii) a cross-over portion extending from the distal end of each of the proximal portions; and
   iv) a clamping portion extending from the distal end of each cross-over portion.

15. A surgical instrument according to claim 14, wherein at least one sidewall of the channel defines the engaging surface.

16. A surgical instrument according to claim 15, wherein the at least one sidewall of the channel defining the engaging surface tapers outwardly towards the distal end of the channel.

17. A surgical instrument according to claim 16, wherein the at least one sidewall includes a pair of sidewalls, each of the sidewalls tapering outwardly towards the distal end of the channel.

18. A surgical instrument according to claim 14, further including a biasing member operably engaging the plunger, the biasing member urging the plunger toward the retracted position.

19. A surgical instrument according to claim 18, wherein the biasing member includes a coil spring.

20. A surgical instrument according to claim 11, wherein the housing includes a pair of finger gripping members positioned at a proximal end thereof.

21. A surgical instrument according to claim 20, wherein the plunger includes an actuator member supported at a proximal end thereof.

22. A surgical instrument according to claim 11, wherein the jaw members each include a recess configured to support a clamp therebetween.

23. A surgical instrument according to claim 22, wherein each recess includes angled sidewalls which intersect at an apex.

24. A surgical instrument according to claim 14, wherein the distal end of each clamping portion includes a sharpened tip.

25. A surgical instrument according to claim 14, wherein each proximal portion includes a dimpled section configured to receive a portion of one of the jaw members of the occlusion clamp applicator.

* * * * *